(12) United States Patent
Dickhans

(10) Patent No.: US 8,398,625 B2
(45) Date of Patent: Mar. 19, 2013

(54) ELECTROSURGICAL ELECTRODE WITH INSULATIVE COATING

(75) Inventor: William J. Dickhans, Longmont, CO (US)

(73) Assignee: Covidien LP, Mansfield, MA (US)

( * ) Notice: Subject to any disclaimer, the term of this patent is extended or adjusted under 35 U.S.C. 154(b) by 605 days.

(21) Appl. No.: 12/552,397

(22) Filed: Sep. 2, 2009

(65) Prior Publication Data
US 2011/0054461 A1 Mar. 3, 2011

(51) Int. Cl.
*A61B 18/18* (2006.01)
(52) U.S. Cl. .............................. 606/33; 606/41; 607/101
(58) Field of Classification Search .................... 606/32, 606/33, 40, 41; 607/100, 101, 115, 145, 607/146, 154
See application file for complete search history.

(56) References Cited

U.S. PATENT DOCUMENTS

| | | | |
|---|---|---|---|
| D253,247 S | 10/1979 | Gill | |
| 4,463,234 A | 7/1984 | Bennewitz | |
| D301,739 S | 6/1989 | Turner et al. | |
| 4,850,353 A | 7/1989 | Stasz et al. | |
| 4,862,890 A | 9/1989 | Stasz et al. | |
| D330,253 S | 10/1992 | Burek | |
| 5,254,117 A | 10/1993 | Rigby et al. | |
| 5,261,905 A * | 11/1993 | Doresey, III | 606/45 |
| 5,380,320 A | 1/1995 | Morris | |
| D370,731 S | 6/1996 | Corace et al. | |
| D384,148 S | 9/1997 | Monson | |
| 5,669,907 A | 9/1997 | Platt, Jr. et al. | |
| 5,702,387 A | 12/1997 | Arts et al. | |
| D393,067 S | 3/1998 | Geary et al. | |
| 5,836,897 A | 11/1998 | Sakurai et al. | |
| D402,030 S | 12/1998 | Roberts et al. | |
| D402,031 S | 12/1998 | Roberts et al. | |
| 5,893,848 A | 4/1999 | Negus et al. | |
| 5,928,159 A | 7/1999 | Eggers et al. | |
| 6,004,318 A * | 12/1999 | Garito et al. | 606/41 |
| 6,066,137 A * | 5/2000 | Greep | 606/45 |
| 6,071,283 A * | 6/2000 | Nardella et al. | 606/46 |
| 6,132,427 A * | 10/2000 | Jones et al. | 606/45 |
| 6,139,547 A | 10/2000 | Lontine et al. | |

(Continued)

FOREIGN PATENT DOCUMENTS

DE 24 29 021 A1 1/1976
DE 24 60 481 A1 6/1976

(Continued)

OTHER PUBLICATIONS

International Search Report EP10175050 dated Dec. 20, 2010.

(Continued)

*Primary Examiner* — Linda Dvorak
*Assistant Examiner* — Jocelyn D Ram

(57) ABSTRACT

An electrode adapted to connect to an electrosurgical instrument is provided. The electrode includes a proximal end that is adapted to connect to an electrosurgical instrument and an electrosurgical energy source. The electrode includes a distal end configured for treating tissue. The distal end of the electrode includes a first portion having one or more edges and a second portion having a substantially blunt profile. An insulative material is disposed over at least the distal end of the electrode. The insulative material includes a first thickness at the first portion and a second thickness at the second portion, wherein upon activation, the insulative material disposed over the first portion breaks away from the first portion allowing energy to travel to tissue from the first portion.

9 Claims, 5 Drawing Sheets

U.S. PATENT DOCUMENTS

| | | | |
|---|---|---|---|
| D433,752 S | 11/2000 | Saravia | |
| D441,077 S | 4/2001 | Garito et al. | |
| 6,241,723 B1 * | 6/2001 | Heim et al. | 606/34 |
| 6,286,512 B1 | 9/2001 | Loeb et al. | |
| 6,287,305 B1 | 9/2001 | Heim et al. | |
| 6,306,135 B1 * | 10/2001 | Ellman et al. | 606/45 |
| 6,325,799 B1 | 12/2001 | Goble | |
| D453,222 S | 1/2002 | Garito et al. | |
| D453,833 S | 2/2002 | Hess | |
| 6,355,034 B2 | 3/2002 | Cosmescu | |
| D457,955 S | 5/2002 | Bilitz | |
| 6,413,255 B1 | 7/2002 | Stern | |
| 6,458,126 B1 * | 10/2002 | Doyle | 606/49 |
| 6,511,479 B2 * | 1/2003 | Gentelia et al. | 606/45 |
| 6,632,193 B1 | 10/2003 | Davison et al. | |
| 6,702,812 B2 | 3/2004 | Cosmescu | |
| D493,530 S | 7/2004 | Reschke | |
| D493,888 S | 8/2004 | Reschke | |
| D494,270 S | 8/2004 | Reschke | |
| D495,051 S | 8/2004 | Reschke | |
| D495,052 S | 8/2004 | Reschke | |
| D515,412 S | 2/2006 | Waaler et al. | |
| D521,641 S | 5/2006 | Reschke et al. | |
| D535,396 S | 1/2007 | Reschke et al. | |
| 8,187,272 B2 * | 5/2012 | Sensenbrenner et al. | 606/50 |
| 8,216,235 B2 * | 7/2012 | Rioux et al. | 606/51 |
| 2003/0014050 A1 * | 1/2003 | Sharkey et al. | 606/45 |
| 2005/0065510 A1 | 3/2005 | Carmel et al. | |
| 2005/0154385 A1 | 7/2005 | Heinm et al. | |
| 2005/0288665 A1 * | 12/2005 | Woloszko | 606/41 |
| 2012/0150178 A1 * | 6/2012 | Durgin et al. | 606/46 |

FOREIGN PATENT DOCUMENTS

| | | |
|---|---|---|
| DE | 30 45 996 | 7/1982 |
| FR | 2235669 | 1/1975 |
| FR | 2798579 | 3/2001 |
| WO | WO 9747249 | 12/1997 |
| WO | WO 0164122 | 9/2001 |
| WO | WO 2004/045436 A1 | 6/2004 |

OTHER PUBLICATIONS

U.S. Appl. No. 12/144,352, filed Jun. 23, 2008, Fry et al.
U.S. Appl. No. 12/144,356, filed Jun. 23, 2008, Kerr.
U.S. Appl. No. 12/144,367, filed Jun. 23, 2008, Heard et al.
U.S. Appl. No. 12/144,372, filed Jun. 23, 2008, Heard et al.
U.S. Appl. No. 12/163,134, filed Jun. 27, 2008, Cunningham et al.
U.S. Appl. No. 12/368,463, filed Feb. 10, 2009, Mathonnet et al.
U.S. Appl. No. 12/394,456, filed Feb. 26, 2009, Kerr et al.
U.S. Appl. No. 12/393,089, filed Feb. 26, 2009, Kerr et al.
International Search Report from PCT-US03-37111; Jul. 21, 2004.
International Search Report from PCT-US04-04685; Aug. 6, 2004.
International Search Report from EP-0401-5980; Sep. 30, 2004.
International Search Report from PCT-US03-22900; Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.
International Search Report from EP 06 00 6908 dated Feb. 25, 2009.
International Search Report from EP 08 02 1070 dated Apr. 1, 2009.
Zucker, Karl, Surgical Laparoscopy, Lippincott Williams & Wilkins, Ed. 2, 2001 (2 pages).

* cited by examiner

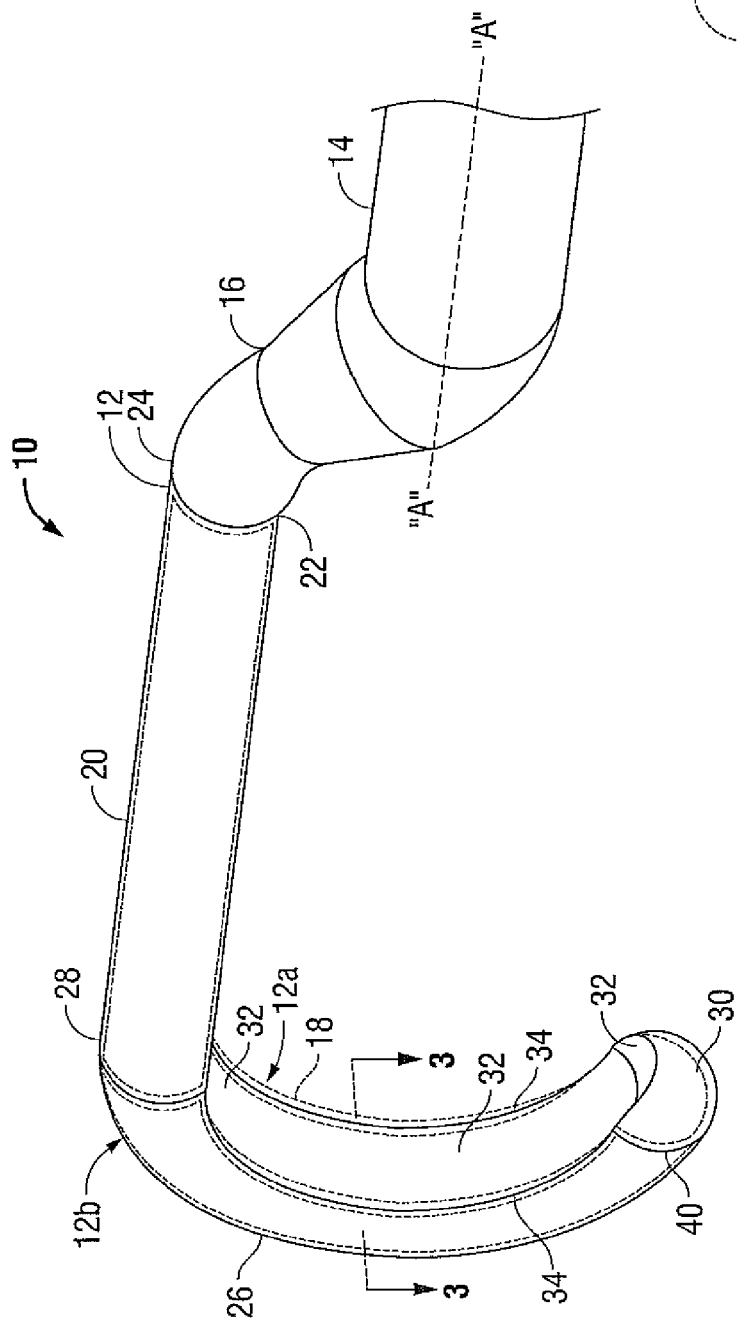
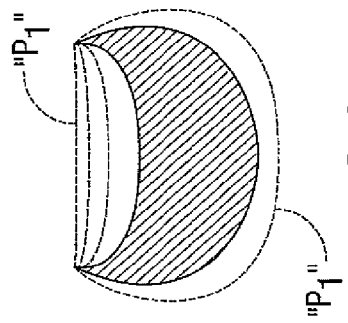
FIG. 2
FIG. 3

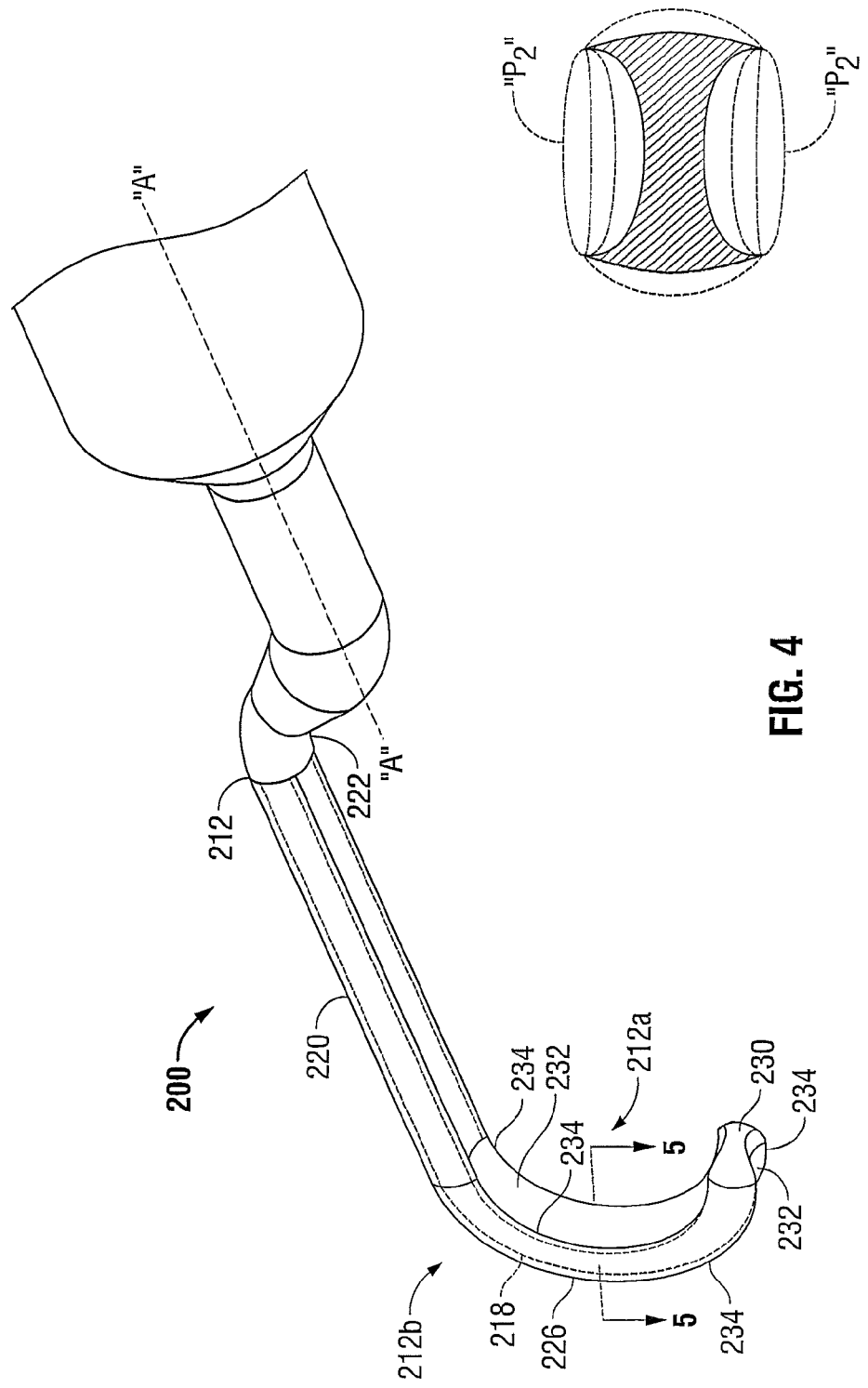

ELECTROSURGICAL ELECTRODE WITH INSULATIVE COATING

BACKGROUND

1. Technical Field

The present disclosure relates to an electrosurgical electrode and, more particularly, to an electrosurgical electrode including an insulative coating configured to provide a path for electrosurgical energy from the electrosurgical electrode to tissue during an electrosurgical procedure.

2. Background of Related Art

Electrosurgical instruments have become widely used by surgeons in recent years. By and large, most electrosurgical instruments are hand-held instruments, e.g., an electrosurgical pencil, which transfer radio-frequency (RF) electrical or electrosurgical energy to a tissue site via an electrosurgical electrode. Typically, the electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

Typically, electrosurgical electrodes configured for electrosurgical use are subject to high temperatures at least where an electrosurgical arc emanates during the electrosurgical procedure, e.g., fulguration or coagulation. In some instances, the heat generated by the electrosurgical electrode during an electrosurgical procedure may cause proteins in bodily fluids and/or tissue to coagulate and adhere to the electrodes. To combat this adhering of bodily fluids and/or tissue to the electrosurgical electrodes, an insulative coating, e.g., a Teflon polymer, may be applied to the electrosurgical electrode.

However, as can be appreciated by one skilled in the art, areas of the electrosurgical electrode covered with an insulative coating cannot transmit RF electrical or electrosurgical energy to a tissue site.

SUMMARY

The present disclosure provides an electrode adapted to connect to an electrosurgical instrument. The electrode includes a proximal end that is adapted to connect to an electrosurgical instrument and an electrosurgical energy source. The electrode includes a distal end configured for treating tissue. The distal end of the electrode includes a first portion having one or more edges and a second portion having a substantially blunt profile. An insulative material is disposed over at least the distal end of the electrode. The insulative material includes a first thickness at the first portion and a second thickness at the second portion, wherein upon activation, the insulative material disposed over the first portion breaks away from the first portion allowing energy to travel to tissue from the first portion.

The present disclosure provides a method for performing an electrosurgical procedure. The method includes providing an electrosurgical system that includes an electrode that includes an insulative coating. A step of the method includes positioning the electrosurgical electrode adjacent a tissue site. The method includes transmitting an initial command signal to an electrosurgical generator in operative communication with the electrosurgical system. The method includes transmitting an RF pulse to the electrode in response to the initial command signal, such that at least a portion of the insulative coating is removed. And, another step of the method includes transmitting RF electrosurgical energy to the electrosurgical electrode such that an electrosurgical effect is achieved at the tissue site.

BRIEF DESCRIPTION OF THE DRAWINGS

Various embodiments of the present disclosure are described hereinbelow with references to the drawings, wherein:

FIG. 2 is an enlarged view of the area of detail of the electrosurgical electrode illustrated in FIG. 1;

FIG. 3 is a cut-away, cross-sectional view taken along line segment 3-3 of FIG. 2;

FIG. 4 is an electrosurgical electrode configured for use with the electrosurgical system of FIG. 1 in accordance with an alternate embodiment of the present disclosure;

FIG. 5 is a cut-away, cross-sectional taken along line segment 5-5 of FIG. 4;

DETAILED DESCRIPTION

Figure 1:
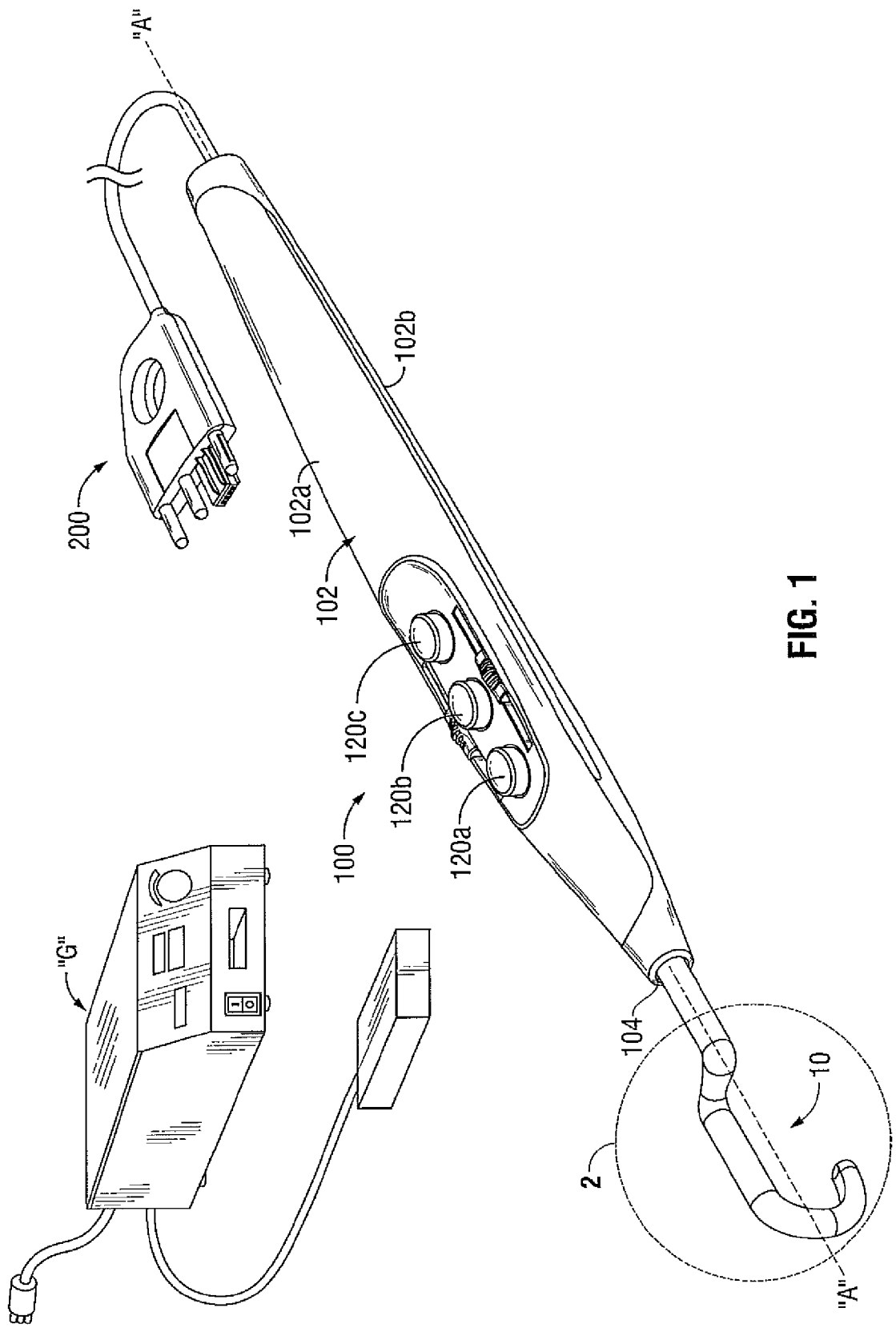
FIG. 1. is a side, perspective view of an electrosurgical system including an electrosurgical electrode in accordance with an embodiment of the present disclosure.

Particular embodiments of the presently disclosed electrosurgical electrode are described in detail with reference to the drawing figures wherein like reference numerals identify similar or identical elements. As used herein, the term "distal" refers to that portion which is further from the user while the term "proximal" refers to that portion which is closer to the user or surgeon.

FIG. 1 sets forth a side, perspective view of an electrosurgical system including an electrosurgical pencil 100 including an electrosurgical electrode 10 constructed in accordance with one embodiment of the present disclosure. While the following description will be directed towards electrosurgical pencils it is envisioned that the features and concepts (or portions thereof) of the present disclosure can be applied to any electrosurgical type instrument, e.g., forceps, suction coagulators, vessel sealers, wands, etc.

As seen in FIG. 1, electrosurgical pencil 100 includes an elongated housing 102 having a top-half shell portion 102a and a bottom-half shell portion 102b. Electrosurgical pencil 100 includes a blade receptacle 104 disposed at a distal end of housing 102 configured to operatively and removably connect to a replaceable electrosurgical electrode 10. Electrosurgical pencil 100 may be coupled to a conventional electrosurgical generator "G" via a plug assembly 200. Electrosurgical pencil 100 includes one or more activation switches (three activation switches 120a-120c are shown). Each activation switch 120a-120c controls the transmission of RF electrical energy supplied from generator "G" to electrosurgical electrode 10.

For a more detailed description of the electrosurgical pencil 100 including operative components associated therewith, reference is made to commonly-owned United States Patent Publication No. 2006/0178667.

With reference now to FIGS. 2 and 3, and initially with reference to FIG. 2, electrosurgical electrode 10 (electrode 10) is shown. Electrode 10 may be fabricated from a conductive type material, such as, for example, stainless steel, or may be coated with an electrically conductive material. Electrode 10 may include any suitable configuration including but not limited to a hook, needle, loop, blade, wand, etc. In the embodiment illustrated in FIGS. 1-5, electrode 10 includes a generally hook or "L" shape with a generally circular cross-section that extends from a proximal end 14 of electrode 10 to a distal end 12 of the electrode 10.

Electrode 10 includes a layer of insulative coating 18 that coats distal end 12 and/or proximal end 14. In embodiments, the layer of insulative coating 18 may be applied evenly over the entire surface of electrode 10. Conversely, insulative coating may be applied in a non-even fashion. More particularly, electrode 10 may include portions (e.g., areas that are intended to emanate electrosurgical energy to a tissue site) that have less insulative coating 18 than other areas of the electrode 10 (e.g., areas that are not intended to emanate electrosurgical energy to a tissue site). More particularly, electrode 10 may include an arcuate cutout 32 that includes a thicker layer of insulative coating 18 and edges 34 that include a thinner layer of insulative coating 18. This configuration of electrode 10 includes an uneven layer of insulative coating 18 that facilitates and/or speeds up the breakdown of insulative coating 18 at or near edges 34. Insulative coating 18 may be made from any suitable material including but not limited to Teflon®, Teflon® polymers, silicone and the like.

As noted above, electrode 10 operatively and removably connects to blade receptacle 104. To this end, proximal end 14 is selectively retained by receptacle 104 within the distal end of housing 102. Reference is again made to commonly-owned United States Patent Publication No. 2006/0178667 for a more detailed description of the operative electrical and/or mechanical interfaces associated with proximal end 14 of electrode 10 and receptacle 104. In embodiments, an articulating portion 16 extends from proximal end 14 and operably connects distal end 12 and proximal end 14 to each other, see FIGS. 2 and 4. The articulating portion 16 allows a user to substantially fix the distal end 12 of electrode 10 in a desired position prior to electrosurgically effecting tissue.

Distal end 12 of electrode 10 extends distally beyond receptacle 104. Distal end 12 includes inner and outer faces 12a and 12b, respectively. Distal end 12 includes an elongated shaft portion 20 having a proximal end 22 that extends from a distal end 24 of the articulating portion 16. In embodiments, shaft portion 20 is disposed parallel with respect to a longitudinal axis "A" of the electrosurgical pencil 100, as best seen in FIG. 2.

Distal end 12 includes a curved portion 26 that extends from a distal end 28 of the shaft 20. Curved portion 26 includes a generally concave configuration. In certain instances, this concave configuration may facilitate manipulating tissue. Curved portion 26 includes a generally circular cross-section. A distal end 40 of curved portion 26 includes a tip 30. In the embodiments illustrated in FIGS. 1-3, tip 30 includes a generally rounded, blunt tip configuration. Conversely, tip 30 may include a generally pointed, sharp tip configuration. Specific tip configurations of tip 30 will depend on the contemplated uses of a manufacturer.

An arcuate cutout 32 extends along the inner face 12a from the tip 30 of the curved portion 26 to the distal end 28 of the shaft 20, as best seen in FIG. 2. Alternatively, the arcuate cutout 32 may extend from the tip 30 to the distal end 24 of articulating portion 16 (see FIG. 4, for example). The specific configuration of arcuate cutout 32 with respect to the distal end 12 and/or shaft 20 will depend on the contemplated surgical purposes of the electrode 10. For example, in embodiments, the arcuate cutout 32 can be extended or reduced along a length of the inner face 12a such that a specific electrosurgical effect can be achieved at a desired location along the inner face 12a.

Arcuate cutout 32 extends along the inner face 12a and defines one or more edges 34. In the embodiment illustrated in FIG. 2, arcuate cutout 32 defines two relatively sharp edges 34. The combination of arcuate cutout 32 and edges 34 provides at least a portion of the distal end 12 of the electrode 10 that includes a region of insulative coating 18 that is configured to provide a path for electrosurgical energy to flow from the distal end 12 of the electrode 10 to tissue during an electrosurgical procedure. More particularly, when electrosurgical energy is transmitted (e.g., in response to an initial command signal) to the distal end 12 of the electrode 10, the edges 34 provide an area of high concentration of electrosurgical energy along the length of the edge 34. This high concentration of electrosurgical energy breaks down or "blows off," e.g., vaporizes, the layer of insulative coating 18 that electrically insulates the edges 34, which, in turn, provides one or more paths "$P_1$" for RF energy to flow, see FIG. 3. The sharpness of edges 34 is directly proportional to the concentration of electrosurgical energy at the edges 34 when electrosurgical energy is transmitted to the electrode 10. That is, the sharper the edges 34 for a given amount of transmitted electrosurgical energy the higher the concentration of electrosurgical energy at the edges 34 when electrosurgical energy is transmitted to the electrode 10. The sharpness of the edges 34 relative to the arcuate cutout 32 will depend on the contemplated uses of a manufacturer.

Electrode 10 including distal end 12 and proximal end 14 may be formed by any suitable techniques, e.g., machining techniques. For example, in embodiments, distal end 12 including arcuate cutout 32 and/or sharp edges 34 may be formed by known milling techniques. Alternatively, or in combination therewith, arcuate cutout 32 and/or sharp edges 34 may be formed by known etching techniques.

With reference to FIGS. 4 and 5, and initially with reference to FIG. 4, an alternate embodiment of electrode 10 is shown designated 200. Electrode 200 is substantially similar to electrode 10. Accordingly, only those features and/or operative components that are unique or distinctive to electrode 200 will be described herein.

Unlike electrode 10, electrode 200 includes a pair of arcuate cutouts 232 that extend along both an inner face 212a and outer face 212b from a tip 230 of the curved portion 226 to the proximal end 222 of the shaft 220. More particularly, arcuate cutouts 232 extend along both the inner face 212a and outer face 212b and define one or more edges 234. In the embodiment illustrated in FIG. 4, arcuate cutouts 232 define four relatively sharp edges 234. The combination of arcuate cutouts 232 and edges 234 provides at least a portion of the distal end 212 of the electrode 200 that includes a region of insulative coating 218 that is configured to provide a path for transmitting electrosurgical energy from the distal end 212 of the electrode 200 to tissue during an electrosurgical procedure. More particularly, when electrosurgical energy is transmitted to the distal end 212 of the electrode 200, the edges 234 provide an area of high concentration of electrosurgical energy along the length of the edge 234. This high concentration of electrosurgical energy breaks down or "blows off," e.g., vaporizes, the layer of insulative coating 218 that electrically insulates the edges 234, which, in turn, provides one or more paths "$P_2$" for RF energy to flow, see FIG. 5. As noted above with respect to edges 34, the sharpness of edges 234 is directly proportional to the concentration of electrosurgical energy at the edges 234 when electrosurgical energy is transmitted to the electrode 200. That is, the sharper the edges 234 the higher the concentration of electrosurgical energy at the edges 234 when electrosurgical energy is transmitted to the electrode 200.

Figure 6:
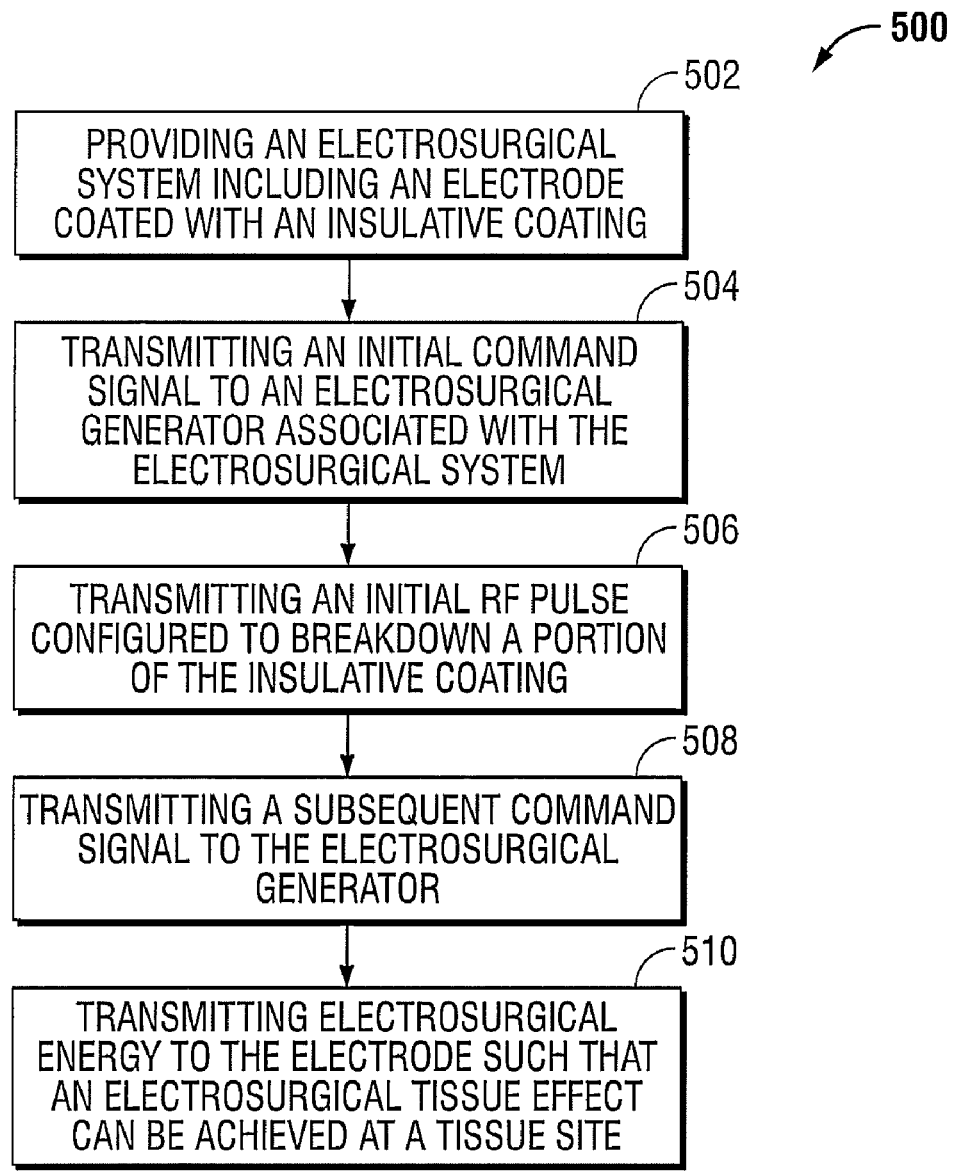
FIG. 6 is a flow chart illustrating steps for performing an electrosurgical procedure in accordance with an embodiment of the present disclosure.

With reference to FIG. 6, a method 500 of use of electrode 10 will be described in terms of use with an electrosurgical system including an electrosurgical pencil 100 coupled to a conventional electrosurgical generator "G" via the plug assembly 200 (step 502). Electrosurgical pencil 100 and/or generator "G" may be set to an initial insulation "breakdown" mode setting. A user may position the curved portion 26 of electrode 10 adjacent a tissue site. One or more of the activation switches 120*a*-120*c* may be employed to transmit an initial command signal to the generator "G" (step 504). In response to receiving the initial command signal, generator "G" may be configured to transmit an initial RF pulse that is configured to breakdown or "blow-off," e.g., vaporize, the insulative coating 18 located at or adjacent the one or more edges 34 (step 506). As noted above, only the insulative coating 18 located at or near the edges 34 is broken-down, and the insulative coating 18 located on the other areas (e.g., arcuate cutout 32) on the electrode 10 remain intact. In an embodiment, once the insulative coating 18 is broken-down or "blown off," e.g., vaporized, one or more of the activation switches 120*a*-120*c* may be employed to transmit a subsequent command signal to the generator "G" (step 508). In response to the subsequent command signal, generator "G" may transmit RF electrosurgical energy to the electrode 10 which emanates from the one or more edges 34 such that an electrosurgical tissue effect may be achieved at the tissue site (step 510). It is contemplated that one skilled in the art will appreciate other methods of use for electrode 10.

Figure 7A:
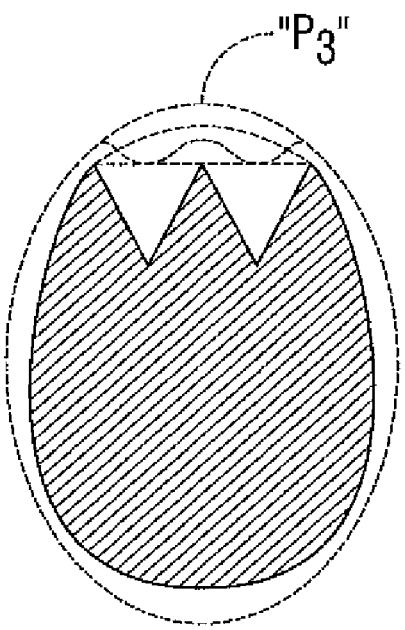
FIGS. 7A and 7B are cross-sectional views illustrating various electrode configurations.
Figure 7B:
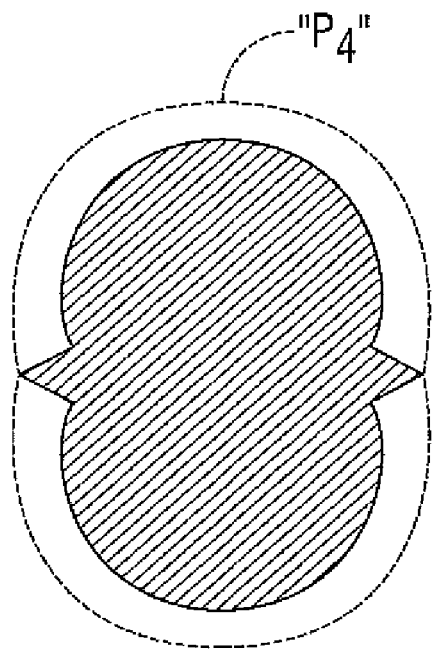

From the foregoing and with reference to the various figure drawings, those skilled in the art will appreciate that certain modifications can also be made to the present disclosure without departing from the scope of the same. For example, electrode 10 may include other geometrical configurations. More particularly, FIGS. 7A and 7B are cut-away views illustrating other various electrode 10 configurations including their associated paths "P₃" and "P₄" for RF energy to flow.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrode adapted to connect to an electrosurgical instrument, the electrode comprising:
    a proximal end adapted to connect to an electrosurgical instrument and an electrosurgical energy source and a distal end configured for treating tissue, the distal end including opposing concave cutouts extending along a length thereof and having a respective pair of edges; and
    an insulative material disposed over at least the distal end of the electrode, the insulative material including a first thickness along each of the pair of edges and a second thickness along the opposing concave cutouts, wherein upon activation, the insulative material vaporizes along each of the pair of edges allowing energy to travel to tissue therefrom.

2. An electrode according to claim 1, wherein the first thickness of the insulative material at each of the pair of edges is less than the second thickness of the insulative material at the opposing concave cutouts.

3. An electrode according to claim 1, wherein the distal end of the electrode includes an inside face and an outside face.

4. An electrode according to claim 3, wherein each of the pair of edges are configured to vaporize the insulative material when the source of electrosurgical energy is activated such that an electrosurgical effect is caused to tissue on the inside and outside faces of the electrode during the electrosurgical procedure.

5. An electrode according to claim 1, wherein the distal end of the electrode is one of hook shaped and "L" shaped.

6. An electrode according to claim 1, wherein the electrode further includes an articulating portion.

7. An electrode according to claim 6, wherein the opposing concave cut-outs extend from a tip of the distal end to the articulating portion of the electrosurgical electrode.

8. An electrode according to claim 1, wherein the electrosurgical electrode is formed via a process selected from milling and etching.

9. A method of performing an electrosurgical procedure, the method including:
    providing an electrosurgical system including an electrode that includes a distal end including opposing concave cutouts extending along a length thereof and having a respective pair of edges, wherein an insulative material is disposed over at least the distal end of the electrode, the insulative material including a first thickness along each of the pair of edges and a second thickness along the opposing concave cutouts;
    positioning the electrode adjacent a tissue site;
    transmitting an initial command signal to an electrosurgical generator in operative communication with the electrosurgical system;
    in response to the initial command signal, transmitting an RF pulse to the electrosurgical electrode such that at least a portion of the insulative coating is vaporized from each of the pair of edges; and
    transmitting RF electrosurgical energy to the electrosurgical electrode such that an electrosurgical effect is achieved at the tissue site.

\* \* \* \* \*